United States Patent [19]

Jeffrey

[11] 3,959,367

[45] May 25, 1976

[54] OXIDATION OF HALO-OLEFINS

[75] Inventor: Gaines C. Jeffrey, Houston, Tex.

[73] Assignee: The Dow Chemical Company, Midland, Mich.

[22] Filed: Mar. 12, 1971

[21] Appl. No.: 123,889

Related U.S. Application Data

[63] Continuation of Ser. No. 715,974, March 26, 1968, abandoned.

[52] U.S. Cl. .................. 260/544 Y; 260/348.5 V; 260/597 R; 260/604 R; 260/687 R
[51] Int. Cl.² ............... C07D 301/06; C07C 51/32; C07C 45/04
[58] Field of Search ............ 260/544 Y, 687, 348.5, 260/2 V, 544 Y, 687, 348.5 V, 597 R, 604 R

[56] References Cited

UNITED STATES PATENTS

| | | | |
|---|---|---|---|
| 1,976,265 | 10/1934 | Mugdan | 260/123 |
| 3,509,210 | 4/1970 | Gaertner, Jr. et al. | 260/544 Y |

OTHER PUBLICATIONS

Erdman – Autooxidation of trichloroethylene, Chemical Abstracts 1912, p. 1140.

*Primary Examiner*—Norman Morgenstern
*Attorney, Agent, or Firm*—Walter J. Lee

[57] ABSTRACT

Process for the non-catalytic liquid phase oxidation of halo-olefins, having 2 to 7 carbon atoms, by $O_2$ at elevated temperatures and pressures to produce oxygenated organic products having the same number of carbon atoms as the starting material.

5 Claims, No Drawings

OXIDATION OF HALO-OLEFINS

Cross-Reference to Related Application

This application is a continuation of copending application Ser. No. 715,974 filed Mar. 26, 1968, now abandoned.

BACKGROUND OF THE INVENTION

This invention relates to a process for oxidizing halo-olefins without the use of an added catalyst, initiator or other external means of initiation.

The oxidation of halo-olefins to obtain epoxides, acyl halides haloketones or haloaldehydes by employing initiators or catalysts such as, for example, gamma radiation, peroxides, and ultraviolet light, especially when the reaction is promoted by adding molecular chlorine, is known. Heretofore it has been thought that the oxidation of such material must be carried out in the presence of one or more of these initiators. (U.S. Pat. No. 2,472,946).

SUMMARY OF THE INVENTION

It has now been found that surprisingly high yields and conversion rates are obtained by simply contacting a liquid halo-olefin with oxygen at a temperature of from 25° to 350°C., and at an oxygen pressure of from 100 to 1200 psi and higher. The oxygen may be employed undiluted, or it may be diluted with other inert gases such as, for example, argon, if desired. Air may also be employed but it should be dry. Generally, pure oxygen is preferred, but diluted oxygen may be used to advantage with highly active haloolefins such as, for example, 1,1-dichloroethylene.

The reaction is characterized by having an induction period, after which the conversion to useful oxygenated products proceeds smoothly. The induction period can be minimized by using halo-olefins which do not contain inhibitory impurities or by adding a more reactive halo-olefin. The induction period is essentially eliminated by filling the reactor with the reaction mixture of a prior oxidation run, then introducing oxygen and the desired halo-olefin.

It has further been found that it is possible to control the start-up of the oxidation of the more reactive halo-olefins such as, for example, 1,1-dichloroethylene, which hitherto have been extremely difficult to oxidize because of the tendency of the reaction to run out of control in the early stages, by feeding the halo-olefin, alone or in admixture with inert or less reactive halo-olefins, into a reaction chamber that contains an inert material or a partially oxidized less reactive halo-olefin and has been brought to the operating conditions before the addition of the undiluted reactive halo-olefin begins. Alternatively, the latter may be fed into a reaction chamber that already contains the reaction products of the controlled oxidation. When oxidizing 1,1-dichloroethylene it is preferred that the operating conditions be such that the conversion of 1,1-dichloroethylene is better than 90%. In this manner the start-up of the reaction proceeds smoothly without an excessive exothermic reaction and the process continues substantially as with other haloolefins.

It has also been found, and it forms a further embodiment of this invention, that halo-olefins that are relatively more inert may be more readily oxidized to higher conversions by co-oxidizing them with a more readily oxidizable halo-olefin. For example, greater conversions of tetrachloroethylene to trichloroacetyl chloride are obtained when the tetrachloroethylene is co-oxidized in admixture with 1,1-dichloroethylene.

Halo-olefins that may be oxidized in accordance with this invention include those containing from 2 to 7 carbon atoms wherein the halogen may be chlorine, fluorine, bromine or iodine. The preferred haloolefins are the 2 to 3 carbon halo-olefins containing a plurality of halogens. Most advantageously the halogen is fluorine or chlorine.

The preferred operating conditions are generally from about 70° to 300°C., and from 300 to 1000 psig of oxygen. These conditions will vary with the properties of the material being oxidized and are interdependent, i.e. at higher temperatures greater pressures may be desirable and vice versa. The temperature and pressure conditions are such that the halo-olefin remains in the liquid state. The conditions will also vary with the properties of the desired end product, for example, lower operating temperatures are preferred if it is desired to isolate the oxides. In starting up the reaction it is best to employ temperatures near the lower end of the above described ranges in order to obtain better conversions of the halo-olefins to the desired oxygenated products.

The process may be run batchwise, continuously or semi-continuously, and in one or more stages, as desired. An excess of oxygen is desired if the operation is continuous, as the excess would be vented with the reaction products. In batch operations, mole ratios of 1:1 of oxygen to halo-olefin are generally preferred, although variations in pressure will give a wide variation in the amount of oxygen in solution. In order to get best results the oxygen should be finely dispersed. This is advantageously accomplished by introducing the oxygen into the reactant in a finely divided state, e.g. through a frit unless other means of agitation are used, such as, for example, fast cycling of the reaction mixture through a pump and back into the reactor. In continuous reactors it has been found that length-to-diameter ratios of from about 4 to 34 are advantageously employed, with the preferred length-to-diameter ratio being about 10 to 20.

In the oxidation of tetrachloroethylene, improved conversions are obtained in a preferred twostage mode of operation that employs two reactors in sequence, preferably with the first reactor having about twice the volume of the second. In this preferred method, the temperature in the first reactor is kept in the range of from 80° to 110°C. and the pressure is from about 500 to 1000 p.s.i.g. In the second reactor the temperature is preferably kept at about 225°–275°C. and the pressure at about 500 to 1000 p.s.i.g. In this preferred process, conversions of over 90 percent are readily obtained. At temperatures above 275°C. in the second reactor the yield of trichloroacetyl chloride is reduced. At temperatures below 225°C. in the second reactor the conversion falls off.

DESCRIPTION OF THE PREFERRED EMBODIMENT

The invention will be further understood by reference to the following examples wherein all percentages are mole percents unless otherwise noted.

EXAMPLE I

A one-liter stainless steel reaction vessel was charged with 800 ml. of stabilized dry cleaning grade (DOW-PER) tetrachloroethylene. An oxygen cylinder was attached to an inlet such that when oxygen was pressured into the reaction vessel it entered the vessel below the surface of the tetrachloroethylene through a stainless steel frit. The vessel was vented at the top for a few seconds to purge out the air above the tetrachloroethylene, then the vent line was blocked and the vessel pressured with oxygen (and simultaneously heated to a temperature of 100°C.) to a pressure of 800 p.s.i.g. The oxygen cylinder was left attached to the reaction vessel with a pressure regulator and check valve between them so that more oxygen would be supplied as the pressure in the reaction vessel dropped below 800 p.s.i.g. No more heat was applied to the reaction vessel during this run. The temperature of the reaction mixture was recorded at intervals and samples for analysis were taken at intervals from an outlet near the bottom of the vessel.

600 p.s.i.g. was employed. The following table described the reaction.

| Reaction Time (Hrs.) | Reaction Temp.°C. | % Conv. | Composition of Conversion Products, % | | | |
|---|---|---|---|---|---|---|
| | | | $CCl_3-COCl$ | $\begin{array}{c}CCl_2-CCl_2\\ \diagdown\diagup\\ O\end{array}$ | $Cl-\overset{\overset{O}{\|}}{\underset{\|}{C}}-Cl$ | $C_2 6$ |
| 0 | ~32 | — | — | — | — | — |
| 8.25 | 36 | 3.0 | 30.5 | 50.8 | 18.7 | 0 |
| 9.0 | 37 | 3.2 | 23.5 | 64.7 | 11.8 | 0 |
| 9.5 | 39 | 4.4 | 39.1 | 36.8 | 24.1 | 0 |
| 9.75 | 42 | 6.7 | 42.4 | 30.6 | 27.2 | 0 |
| 10.17 | 52 | 8.5 | 49.4 | 24.2 | 26.5 | 0 |
| 10.5 | 134 | 25.7 | 54.5 | 17.5 | 27.3 | 0.8 |
| 11.0 | 130 | 32.0 | 62.4 | 12.7 | 24.0 | 1.0 |
| 12.0 | 110 | 41.5 | 68.1 | 10.0 | 21.9 | 0.8 |
| 13.0 | 90 | 42.6 | 84.0 | 1.2 | 14.0 | 0.7 |
| 14.0 | 74 | 45.0 | 81.2 | 1.9 | 16.2 | 0.7 |
| 15.0 | 64 | 47.4 | 79.2 | 2.1 | 18.1 | 0.7 |

EXAMPLE 2

Using the same reaction vessel and equipment hook-up as in Example 1 above, oxygen was pressured into stabilized tetrachloroethylene to a pressure of 500 p.s.i.g. at ambient temperature (~30°C.). The reaction exothermed to about 125°C. after about 18 hours of contact time and thereafter dropped slowly to ambient temperature. A sample was taken after 24 hours and conversion of the $C_2Cl_4$ was found to be 42.8%. The yield was 81% of trichloroacetyl chloride.

This run was repeated using fresh unstabilized tetrachloroethylene and 600 p.s.i.g. oxygen pressure. An exotherm of 147°C. was observed in 5 hours. Trichloroacetyl chloride was produced in good yield.

EXAMPLE 3

The experiment of Example 2 was repeated using stabilized tetrachloroethylene except that a pressure of

EXAMPLE 4

Stabilized tetrachloroethylene was oxidized continuously, without catalyst addition, in a series of runs, to determine the effect of reaction temperature. Oxidations were conducted in a 1000 ml. stainless steel reactor equipped with an inlet and outlet, means of temperature measurement and control, means of pressure control, means of oxygen dispersion, facilities for sampling reaction products and suitable safety devices. In all runs, tetrachloroethylene was continuously metered into the reactor inlet at a rate of 8.33 ml./min.; giving an average contact time of 2 hours. Oxygen was continuously metered into the reactor inlet through a frit at a ratio of 1 mole of oxygen per mole of tetrachloroethylene. Excess oxygen was vented from the reactor outlet along with the reactor effluent. Reactor pressure was controlled at 800 p.s.i.g. for all runs. Samples of the reactor effluent were collected, in a cold-trap, from the reactor outlet on an hourly basis during each run. Samples were analyzed by gasliquid chromatography to determine the progress of the reaction. Each run was continued for several hours after reaction equilibrium had been reached. Representative samples were then analyzed by mass spectrometry. The following table shows the results of five runs, under equilibrium conditions, will all reaction conditions being constant except that of temperature, which was as designated.

| Time (Min.) | Reaction Temp. °C. | % Conv. | Composition of Conversion Products, % | | | |
|---|---|---|---|---|---|---|
| | | | $CCl_3-COCl$ | $\begin{array}{c}CCl_2-CCl_2\\ \diagdown\diagup\\ O\end{array}$ | $Cl-\overset{\overset{O}{\|}}{\underset{\|}{C}}-Cl$ | $C_2Cl_6$ |
| 5 | 105 | — | — | — | — | — |
| 10 | 124 | 3.2 | 15.6 | 78.1 | 6.3 | 0.1 |
| 20 | 155 | 16.0 | 33.7 | 57.2 | 8.6 | 0.6 |
| 30 | 225 | 23.4 | 56.4 | 32.2 | 11.5 | 0.1 |
| 40 | 212 | 34.5 | 76.4 | 14.9 | 8.6 | 0.1 |
| 50 | 193 | 46.4 | 87.1 | 5.1 | 7.8 | 0.1 |
| 60 | 173 | 52.7 | 86.8 | 5.9 | 7.1 | 0.2 |
| 90 | 130 | 53.3 | 89.8 | 2.3 | 7.6 | 0.2 |

| Reaction Temperature (°C.) | $Cl_2C=CCl_2$ Conv. (%) | $Cl_3C-\overset{O}{\overset{\|}{C}}Cl$ Yield (%) | $Cl_2\overset{O}{\overset{/\backslash}{C}}-CCl_2$ Yield (%) | $COCl_2$ Yield (%) |
|---|---|---|---|---|
| 60 | 2.3 | 46.1 | 35.9 | 18.0 |

-continued

| Reaction Temperature (°C.) | $Cl_2C=CCl_2$ Conv. (%) | $Cl_3C-\overset{O}{\overset{\|}{C}}Cl$ Yield (%) | $Cl_2\overset{O}{\overset{/\backslash}{C}}-CCl_2$ Yield (%) | $COCl_2$ Yield (%) |
|---|---|---|---|---|
| 80 | 18.9 | 48.8 | 38.2 | 13.1 |
| 100 | 23.3 | 74.1 | 15.9 | 9.9 |
| 120 | 13.0 | 89.5 | 0 | 10.6 |
| 130 | 2.0 | 86.3 | 0 | 13.7 |

EXAMPLE 5

Stabilized tetrachloroethylene was oxidized continuously, without catalyst addition, in a series of runs and in the manner of Example 4, except that the single reactor was replaced with two equal volume, stainless steel reactors connected in series. The two reactors (the first reactor designated R-I and the second, R-II) were equipped with independent temperature controls. The effect of R-I temperature was determined at two R-II temperatures in a series of 8 runs conducted under otherwise the same conditions of Example 4. Results are tabulated below.

| Effect of R-I Temperature (R-II=120°C.) | | | | |
|---|---|---|---|---|
| R-I Temperature (°C.) | % Conv. | $Cl_3C-\overset{O}{\overset{\|}{C}}Cl$ Yield (%) | $Cl_2\overset{O}{\overset{/\backslash}{C}}-CCl_2$ Yield (%) | $COCl_2$ Yield (%) |
| 60 | 1.4 | 75.8 | 5.8 | 18.3 |
| 80 | 24.7 | 86.0 | 4.5 | 9.6 |
| 100 | 26.3 | 88.8 | 1.2 | 9.9 |
| 120 | 13.0 | 89.5 | 0 | 10.6 |

| Effect of R-I Temperature (R-II=170°C.) | | | | |
|---|---|---|---|---|
| R-I Temperature (°C.) | % Conv. | $Cl_3C-\overset{O}{\overset{\|}{C}}Cl$ Yield (%) | $Cl_2\overset{O}{\overset{/\backslash}{C}}-CCl_2$ Yield (%) | $COCl_2$ Yield (%) |
| 60 | 36.7 | 90.4 | 0 | 9.6 |
| 80 | 39.1 | 90.8 | 0 | 9.7 |
| 100 | 36.9 | 88.6 | 0 | 11.4 |
| 120 | 4.4 | 84.8 | 0 | 15.2 |

EXAMPLE 6

Stabilized tetrachloroethylene was oxidized continuously, without catalyst addition, in a series of runs and in the manner of Examples 4 and 5 except that the volumes of the two reactors, R-I and R-II, were varied with the total volume being constant.

Constant reaction conditions employed were:

| | |
|---|---|
| R-I Temperature | 100°C. |
| R-II Temperature | 150°C. |
| Reactor pressure | 1000 psig |
| Total Reactor contact time | 6.2 hrs. |

The results of 3 runs are tabulated below.

| Effect of R-I/R-II Volume Ratio | | | | |
|---|---|---|---|---|
| R-I/R-II Volume Ratio | $Cl_2C=CCl_2$ Conv. (%) | $Cl_3C-\overset{O}{\overset{\|}{C}}Cl$ Yield (%) | $Cl_2\overset{O}{\overset{/\backslash}{C}}-CCl_2$ Yield (%) | $COCl_2$ Yield (%) |
| 0.33 | 27.0 | 87.4 | 0 | 12.6 |
| 1.0 | 40.8 | 92.0 | 0 | 8.0 |
| 2.0 | 53.5 | 91.7 | 0 | 8.3 |

EXAMPLE 7

Stabilized tetrachloroethylene was oxidized continuously, without catalyst addition, in a series of runs conducted in the manner of Examples 4 and 5 to determine the effect of R-II temperature. Constant reaction conditions employed were:

| | |
|---|---|
| R-I temperature | 100°C. |
| Total reactor contact time | 5.9 hrs. |
| Reactor pressure | 1000 psig |
| Volume ratio, R-I/R-II | 2/1 |

The results of 10 runs in which R-II temperature was varied are shown in the following table.

| Effect of R-II Temperature | | | | |
|---|---|---|---|---|
| R-II Temperature (°C.) | $Cl_2C=CCl_2$ Conv. (%) | $Cl_3C-\overset{O}{\overset{\|}{C}}Cl$ Yield (%) | $\overset{O}{\overset{/\backslash}{C}}Cl_2$ Yield (%) | $Cl_3C-CCl_3$ Yield (%) |
| 100 | 42.7 | 92.1 | 7.5 | 0.4 |
| 125 | 48.0 | 92.0 | 7.7 | 0.3 |
| 150 | 53.5 | 91.7 | 8.0 | 0.3 |
| 175 | 65.3 | 92.7 | 7.1 | 0.2 |
| 200 | 79.0 | 92.7 | 6.8 | 0.5 |
| 225 | 80.9 | 90.7 | 8.9 | 0.4 |
| 250 | 85.1 | 94.0 | 5.4 | 0.6 |
| 275 | 86.1 | 90.1 | 7.1 | 2.8 |
| 300 | 85.0 | 86.6 | 8.3 | 5.1 |
| 325 | 81.5 | 79.4 | 9.0 | 11.6 |

EXAMPLE 8

Stabilized tetrachloroethylene was oxidized continuously, without catalyst addition, in a series of runs conducted in the manner of Examples 4 and 5, to determine the effect of reactor contact time. Constant reaction conditions employed were:

| | |
|---|---|
| R-I Temperature | 100°C. |
| R-II Temperature | 275°C. |
| Reactor pressure | 1000 psig |
| Volume ratio, R-I/R-II | 2/1 |

The results of 5 runs, in which the total reactor contact time was varied are shown below.

| Effect of Reactor Contact Time | | | | |
|---|---|---|---|---|
| Total Reactor Contact Time (Hrs.) | Conv. (%) | $Cl_3C-\overset{O}{\overset{\|}{C}}Cl$ Yield (%) | $Cl_2\overset{O}{\overset{/\backslash}{C}}-CCl_2$ Yield (%) | $COCl_2$ Yield (%) |
| 4 | 73.8 | 85.3 | 0.4 | 11.3 |
| 5.7 | 80.9 | 89.1 | 0.2 | 7.5 |
| 7.4 | 85.8 | 94.5 | 0.2 | 4.9 |
| 10.7 | 87.0 | 87.5 | 0.1 | 9.0 |
| 18.5 | 90.2 | 89.4 | 0 | 7.3 |

EXAMPLE 9

Stabilized tetrachloroethylene was oxidized continuously, without catalyst addition, in a series of runs conducted in the manner of Examples 4 and 5 except that the reactor oxygen pressure was varied. Constant reaction conditions employed for the first 3 runs were:

| | |
|---|---|
| R-I Temperature | 100°C. |
| R-II Temperature | 275°C. |
| Total Reactor Contact Time | 6 hrs. |
| Volume ratio, R-I/R-II | 2/1 |

Reaction conditions employed for the last run are as indicated in the footnote. Results of the 4 runs are shown below.

Effect of Reactor Pressure

| Reactor Pressure (p.s.i.g.) | $Cl_2C=CCl_2$ Conv. (%) | $Cl_3C-\overset{O}{\overset{\|}{C}}Cl$ Yield (%) | $Cl_2\overset{O}{\overset{/\backslash}{C}-CCl_2}$ Yield (%) | $COCl_2$ Yield (%) |
|---|---|---|---|---|
| 1000 | 86.1 | 90.1 | 0 | 7.1 |
| 700 | 64.8 | 90.3 | 1.8 | 7.9 |
| 400 | 41.6 | 86.7 | 5.1 | 8.2 |
| 400* | 21.2 | 71.5 | 18.4 | 8.3 |

*R-I temp. = R-II temp. = 100°C., contact time = 4 hrs.

EXAMPLE 10

Trichloroethylene was oxidized, without catalyst addition, in a batch reaction system which consisted of a 300 ml. nickel reactor equipped with means of temperature measurement and control, means of agitation, facilities for the continuous introduction of oxygen during reaction and suitable safety devices. Oxygen was fed to the reactor from a calibrated supply cylinder. The reactor was charged with trichloroethylene, purged free of air with oxygen, pressured and checked for a period of 30 min. to assure no oxygen consumption or leakage in the system. The reactor was then depressured and the temperature and pressure brought up to operating conditions simultaneously to avoid overpressuring. Pressure readings on the oxygen supply cylinder were recorded frequently during the reaction and the rate of oxygen consumption (hence, the oxidation rate) determined. The system was such that as little as 0.1 gm of oxygen consumption could be detected.

At the end of the reaction the reactor was chilled, opened and its contents transferred to a sample bottle. Samples were then analyzed by gas-liquid chromatography, mass spectrometry and infra-red spectroscopy.

According to the above procedure, 200 gms of trichloroethylene was charged to the reactor and oxidized under conditions of 100°C. and 100 p.s.i.g. Data showing the progress of the reaction are shown in the following table.

Oxidation of Trichloroethylene at 100°C. and 100 p.s.i.g.

| Reaction Time (Min.) | Oxygen Consumed By Reaction (grams) |
|---|---|
| 0 | 0 |
| 10 | 0 |
| 15 | 0.14 |
| 30 | 1.08 |
| 45 | 2.44 |
| 60 | 4.07 |
| 75 | 4.88 |
| 90 | 5.15 |
| 105 | 5.28 |
| 150 | 5.42 |

Analysis of the reaction products showed that 25.9% of the trichloroethylene was converted to yield 33.2% trichloroethylene oxide, 42.2% dichloroacetyl chloride, 19.1% trichloroacetaldehyde and 5.5% phosgene.

EXAMPLE 11

Trichloroethylene was oxidized continuously, without catalyst addition, using the equipment and procedure described in Example 4. Approximately 30 runs were made for the purpose of studying the reaction variables. One such run was conducted under conditions of 200°C., 400 p.s.i.g. and a 5 hr. contact time. Product analysis by mass spectrometry gave the following results.

| | |
|---|---|
| Unreacted trichloroethylene | 2.5 |
| Trichloroacetaldehyde | 8.5 |
| Dichloroacetyl chloride | 28.5 |
| Dichloromaleic anhydride | 0.2 |
| 2(1,2,2,2-tetrachloroethoxy) chloroacetyl chloride | 8.7 |
| Chloroform | 0.8 |
| Various oxygen-free products | 50.8 |

The conversion of trichloroethylene was found to increase with increased reactor pressure and/or increased reactor contact time. Dichloroacetyl chloride and trichloroacetaldehyde were found to form at the expense of trichloroethylene oxide at higher temperatures.

EXAMPLE 12

1,1-Dichloroethylene was oxidized continuously, without catalyst addition, in the equipment and manner as described in Example 4. Reaction conditions employed were: 105°C. reaction temperature, 500 p.s.i.g. reactor pressure and 2.2 hr. reactor contact time. The reactor initially contained perchloroethylene and its oxidation products from a preceding run. The reactor was brought up to operating conditions and 1,1-dichloroethylene feed and oxygen feed were started to the reactor. The reaction was continued until all tetrachloroethylene and its oxidation products were swept from the reactor and then continued until the reaction reached equilibrium conditions. Samples were then collected from the reactor outlet and analyzed by mass spectrometry. Analytical results showed that 99.8% of the 1,1-dichloroethylene fed was converted to yield 89.7% monochloroacetyl chloride and 2.7% phosgene.

EXAMPLE 13

1,1-Dichloroethylene was oxidized continuously, without catalyst addition, in the manner of Example 12, except that the reactor was lined with Teflon and the oxygen tube and frit were of Teflon, thus excluding all metals from the reaction zone. The temperature employed was 100°C., the pressure was 150 p.s.i.g. and the contact time as 1.6 hours. The conversion was 98.3% with a 96.5% yield of chloroacetyl chloride and 2.9% phosgene.

EXAMPLE 14

1,1-Dichloroethylene was oxidized under the same conditions as Example 12 except at a reaction temperature of 90°C. and with the products of Example 12 in the reactor initially. The reaction was continued for 12 hrs. Analysis of samples showed that 99.5% of the 1,1-dichloroethylene fed to the reactor was converted to yield 89.3% monochloroacetyl chloride and 3.4% phosgene.

Great difficulty was encountered in trying to start-up initially with only 1,1-dichloroethylene and oxygen due to the explosive nature of the mixture. By first filling the reactor with any of a variety of other suitable materials, one can then begin feeding 1,1-dichloroethylene and oxygen to the reactor without difficulty.

EXAMPLE 15

Cis- and trans- 1,2-dichloroethylenes were oxidized without catalyst addition, using the same equipment and in the same manner as described in Example 10. The reactor was charged with 200 grams of 1,2-dichloroethylene which was comprised of 60% of the cis- isomer and 40% of the trans- isomer. Reaction conditions employed were 100°C. and 100 p.s.i.g. The reaction was continued for 2.5 hrs. Reaction products were identified and analyses made by gas-liquid chromatography, infra-red spectroscopy and mass spectrometry. Analytical results showed that 6.0% of the 1,2-dichloroethylene charged was converted to yield 68.5% trans-1,2-dichloroethylene oxide, 14.1% cis-1,2-dichloroethylene oxide and 15.8% dichloroacetaldehyde. The 1,2-dichloroethylene oxides were isolated by gas-liquid chromatography and their I.R. spectra obtained.

EXAMPLE 16

2,3-Dichloropropene was oxidized, without catalyst addition, using the equipment and in the manner of Example 10. The reactor was charged with 50 grams of 2,3-dichloropropene. Reaction conditions employed were 80°C. and 150 p.s.i.g. the progress of the reaction is shown in the following table.

| Reaction Time (minutes) | Oxygen Consumed by the Reaction (grams) |
|---|---|
| 21 | 0 |
| 23 | 0.30 |
| 35 | 0.60 |
| 50 | 1.06 |
| 60 | 1.36 |
| 90 | 1.96 |
| 108 | 2.27 |
| 145 | 2.57 |
| 160 | 2.72 |

Oxygen consumed corresponded to 37.7% conversion of 2,3-dichloropropene based on 1/2 mole oxygen/mole of 2,3-dichloropropene.

Sample analysis showed 1,3-dichloropropanone as the only major reaction product.

EXAMPLE 17

Cis- and trans-1,2,3-trichloropropenes were oxidized, without catalyst addition, using the equipment and in the manner described in Example 10. The reactor was charged with 100 grams of 1,2,3-trichloropropene which was comprised of 47.5% of the trans- isomer and 52.0% of the cis- isomer. Reaction conditions employed were 100°C. and 150 p.s.i.g. The progress of the reaction is shown in the following table.

| Reaction Time (minutes) | Oxygen Consumed by the Reaction (grams) |
|---|---|
| 9 | 0 |
| 12 | 0.29 |
| 15 | 0.57 |
| 20 | 0.86 |
| 25 | 1.00 |
| 35 | 1.14 |
| 240 | 1.48 |

Gas-liquid-chromatographic (G.L.C.) analysis of the reaction product showed 15.7% conversion of the 1,2,3-trichloropropene to three major products. Analysis also showed that the trans- isomer was oxidized to a greater extent than the cis- isomer.

Identification of these products by the combined use of G.L.C., mass spectrometry and infra-red spectroscopy showed the following products in decreasing order of concentration: 2,2,3-trichloropropanol; 1,1,3-trichloropropanone; chloroacetyl chloride; dichloroacetyl chloride; and chloroform.

EXAMPLE 18

1,1,2,3-Tetrachloropropene was oxidized without catalyst addition, using the equipment and in the manner described in Example 10. The reactor was charged with 50 grams of tetrachloropropene. Reaction conditions employed were 150°C. and 150 p.s.i.g. The run was ended after 1 hr. 35 min. reaction time. G.L.C. analysis of the reaction products showed 16.6% conversion of the tetrachloropropene to three major products. Further analysis indicated the following products in decreasing order of concentration: 1,1,1,3-tetrachloropropanone; chloroacetyl chloride; 1,1,2-trichloropropionyl chloride; dichloroacetyl chloride; chloroform and phosgene.

EXAMPLE 19

Trans-1,4-dichloro-2-butene was oxidized, without catalyst addition, using the equipment and in the manner described in Example 10. The reactor was charged with 35 grams of trans-1,4-dichloro-2-butene. Reaction conditions employed were 100°C. and 150 p.s.i.g. The progress of the reaction is shown in the following table.

| Reaction Time (minutes) | Oxygen Consumed by Reaction (grams) | Remarks |
|---|---|---|
| 3 | 0.50 | Run started reaction exothermed to 115°C. |
| 5 | 1.10 | reaction exothermed to 165°C. |
| 7 | 1.64 | reaction temperature 140°C. |
| 9 | 1.78 | reaction temperature 125°C. |
| 10 | 1.92 | reaction temperature 115°C. |
| 15 | 2.06 | reaction temperature 100°C. |
| 18 | 2.19 | Run ended. |

Oxygen consumption indicated 48.8% conversion of trans-1,4-dichloro-2-butene, based on 1/2 mole oxygen/mole trans-1,4-dichloro-2-butene.

Analysis of reaction products indicated the following products in decreasing order of concentration: chlorohydroxybutanol; 1,3,4-trichloro-2-butanone; chlorobutanol; chloroacetaldehyde and dichlorobutanone.

EXAMPLE 20

Tetrachloroethylene was oxidized continuously, without catalyst addition, in the manner of Example 4 under conditions of 100°C., 400 p.s.i.g. and using a 4-hr. reactor contact time. The run was continued for about 18 hrs. Under reaction equilibrium, sample analysis by G.L.C. showed the following results:

| $Cl_2C=CCl_2$ Conv. % | $Cl_3C-\overset{O}{\overset{\|}{C}}Cl$ Yield (%) | $Cl_2\overset{O}{\overset{/\backslash}{C}-CCl_2}$ Yield (%) | $COCl_2$ Yield (%) |
|---|---|---|---|
| 21.2 | 71.5 | 18.4 | 8.3 |

The above run was continued except that the reactor feed was switched to a mixture comprised of 23.2% 1,1-dichloroethylene and 76.8% tetrachloroethylene. After only 1 hr. continued run time the tetrachloroethylene conversion increased to 58.2%. The run was continued for about 8 hrs. Under reaction equilibrium conditions the following results were obtained:

| $Cl_2C=CCl_2$ Conv. (%) | $Cl_3C-\overset{O}{\overset{\|}{C}}Cl$ Yield (%) | $Cl_2\overset{O}{\overset{/\backslash}{C}-CCl_2}$ Yield (%) | $COCl_2$ Yield (%) |
|---|---|---|---|
| 80.8 | 90.1 | 0 | 9.9 |

About 99% of the 1,1-dichloroethylene was converted to yield about 90% chloroacetyl chloride.

EXAMPLE 21

1,2-Dichloroethylene was oxidized continuously, without catalyst addition, in the manner of Example 5 and under conditions of 100°C. R-I temperature, 150°C. R-II temperature, 300 p.s.i.g. and using an 8 hr. reactor contact time. The run was continued for about 24 hrs. Under reaction equilibrium conditions only about 2% of the 1,2-dichloroethylene was converted to yield primarily 1,2-dichloroethylene oxide and dichloroacetaldehyde.

The above run was repeated under the same conditions except using a feed mixture comprised of 50% 1,2-dichloroethylene and 50% tetrachloroethylene. The run was continued for about 22 hours. Under reaction equilibrium conditions 34.2% of the 1,2-dichloroethylene was converted to yield primarily 1,2-dichloroethylene oxide and dichloroacetaldehyde. At the same time, about 30% of the tetrachloroethylene was converted to yield 93.3% trichloroacetyl chloride.

EXAMPLE 22

Using the equipment in the manner described in Example 10, an attempt was made to oxidize 3-chloropropene under conditions of 80°C. and 150 p.s.i.g. The run was allowed to continue for about 18 hrs., during which time no appreciable oxygen consumption was observed.

The reaction exhibited strong inhibition due to impurities in the 3-chloropropene. Sample analysis showed less than 1% conversion of the 3-chloropropene.

The above run was repeated except that 0.1% 1,1-dichloroethylene was added to the 3-chloropropene reactor charge. After an induction time of about 1 hr. oxygen consumption began. The reaction was allowed to continue for about 18 hrs. after which time the oxygen consumed indicated 39.6% conversion of the 3-chloropropene based on 0.5 mole oxygen per mole of 3-chloropropene.

EXAMPLE 23

Stabilized tetrachloroethylene was oxidized, without catalyst addition, using the equipment and in the manner described in Example 10, under conditions of 100°C. and 150 p.s.i.g. The reactor was fitted with means of remote sampling and means of purging oxygen through the reaction medium and venting from the reactor. Small samples were removed from the reactor periodically and analyzed. The reaction was allowed to continue for a period of 18 hrs. at which time analyses indicated that tetrachloroethylene conversion was remaining constant at about 25% with 83.4% yield to trichloroacetyl chloride, 7.4% yield to tetrachloroethylene oxide and 9.2% yield to phosgene. At this time oxygen was gently purged through the reactor for about 5 minutes to remove the major portion of accumulated phosgene and the reaction then continued. Sample analysis showed tetrachloroethylene conversion to immediately increase and after about two hours to again remain constant at about 32% conversion of tetrachloroetylene with similar product yields. The reaction was continued for an additional 16 hours during which time oxygen was continuously purged through the reactor at a low rate. Conversion steadily increased during this time and analysis of the final products indicated about 98% conversion of the tetrachloroethylene and about 97% yield to trichloroacetyl chloride.

EXAMPLE 24

Tetrachloroethylene is continuously oxidized in a three stage reactor system at a pressure of about 800 p.s.i.g. wherein the temperature of the first reactor is about 100°C., the temperature of the second reactor is 250°C. and the temperature of the third reactor is 150°C. A vapor space is maintained in the top of each reactor, product is removed from the bottom of each reactor and a continuous purge of oxygen is maintained through each reactor, with the excess oxygen and phosgene vented from the top of each reactor. In this system conversion of about 98% can be obtained in six hours.

EXAMPLE 25

Tribromoethylene was oxidized, without catalyst addition, using the equipment and in the manner described in Example 10. The reactor was charged with 90 grams (0.3399 mole) of tribromoethylene. The reaction was started at 27°C. and at a pressure of 150 p.s.i.g. No heat was applied. The progress of the reaction is shown in the following table.

| Reaction Time (Minutes) | Oxygen Consumed by Reaction (grams) | Remarks |
|---|---|---|
| 2 | 0.30 | reaction temp. began increasing |
| 3 | 0.74 | reaction temp. at 50°C. |

-continued

| Reaction Time (Minutes) | Oxygen Consumed by Reaction (grams) | Remarks |
|---|---|---|
| 4 | 1.48 | |
| 5 | 2.07 | reaction temp. at 55°C. |
| 8 | 2.52 | reaction temp. at 60°C. |
| 12 | 2.66 | run ended temp. at 60°C. |

Based on oxygen consumption, 48.9% conversion of tribromoethylene was obtained (assuming 0.5 mole oxygen per mole of tribromoethylene charged). Sample analysis by G.L.C. indicated about 50% conversion of tribromoethylene.

The product was analyzed by the combined use of G.L.C., mass spectroscopy and infra-red techniques and the oxidation products were identified as:
 dibromoacetyl bromide
 tribromoacetaldehyde, and
 methyl dibromoacetate.

In accordance with this invention, other halo-olefins such as fluoro-olefins, fluoro-chloro-olefins, chloro-bromo-olefins and fluoro-bromo-olefins were also converted to useful oxygenated products. For example, hexafluoropropene is oxidized to hexafluoropropanone and pentafluoropropionyl fluoride, chlorodifluoroacetyl chloride is obtained by the oxidation of 1,1-dichloro-2,2-difluoroethylene and fluorodichloroacetyl fluoride is obtained by the oxidation of 1,2-dichloro-1,2-difluoroethylene.

Various modifications may be made in the present invention without departing from the spirit or scope thereof and it is understood that I limit myself only as defined in the appended claims.

I claim:

1. A process for the liquid phase oxidation of polyhaloolefins having from 2 to 7 carbon atoms to obtain oxidation products having the same number of carbon atoms as the starting material, said process comprising heating the polyhalo-olefin in admixture with oxygen at temperatures of from about 70°C to about 300°C and $O_2$ pressures of from about 100 to 1200 p.s.i.g. in the absence of an added catalyst, said process being carried out in two stages in two reactors connected in series wherein the first reactor has a volume of about twice that of the second reactor.

2. Process of claim 1 wherein the temperature in the first reactor is in the range of from about 80°C to about 110°C and the temperature in the second reactor is in the range of about 225°C to about 275°C.

3. A process for the liquid phase oxidation of a mixture of two halo-olefins having from 2 to 7 carbon atoms to obtain oxidation products having the same number of carbon atoms as the starting material, said process comprising heating the mixture of halo-olefins in admixture with oxygen at temperatures of from about 70°C to about 300°C and $O_2$ pressures of from about 100 to 1200 p.s.i.g. in the absence of an added catalyst.

4. A process for the liquid phase oxidation of a mixture of tetrachloroethylene and 1,1-dichloroethylene to obtain oxidation products containing two carbon atoms, said process comprising heating the mixture in admixture with oxygen at temperatures of from about 70°C to about 300°C and $O_2$ pressures of from about 100 to 1200 p.s.i.g. in the absence of an added catalyst.

5. A process for the liquid phase oxidation of tetrachloroethylene to obtain trichloroacetyl chloride comprising heating, in the absence of an added catalyst, a mixture of tetrachloroethylene and oxygen in a first reactor at a temperature in the range of about 80°C to about 110°C at a pressure in the range of about 500 to about 1000 p.s.i.g., then further heating the mixture in a second reactor at a temperature in the range of about 225°C to about 275°C at a pressure of about 500 to about 1000 p.s.i.g.

* * * * *

UNITED STATES PATENT OFFICE
CERTIFICATE OF CORRECTION

PATENT NO. : 3,959,367
DATED : May 25, 1976
INVENTOR(S) : Gaines C. Jeffrey

It is certified that error appears in the above-identified patent and that said Letters Patent are hereby corrected as shown below:

Col. 1, line 14, insert a comma after "halides" and "haloketones".

Col. 4, line 8, "Cl-C-" should be --Cl-C-Cl--, delete "C-Cl".

Col. 4, line 8, "$C_2 6$" should be --$C_2Cl_6$--.

Col. 4, line 61, "will" should read --with--.

Col. 12, line 33, "chloroetylene" should read --chloroethylene--.

Signed and Sealed this

Twelfth Day of October 1976

[SEAL]

Attest:

RUTH C. MASON
Attesting Officer

C. MARSHALL DANN
Commissioner of Patents and Trademarks